(12) United States Patent
Ahn et al.

(10) Patent No.: US 7,582,612 B2
(45) Date of Patent: *Sep. 1, 2009

(54) MULTI-ACTION ANTHELMINTIC FORMULATIONS

(75) Inventors: Albert Ahn, Short Hills, NJ (US); Ian Cottrell, Basking Ridge, NJ (US)

(73) Assignees: Hartz Mountain Corporation, Secaucus, NJ (US); Virbac Corporation, Fort Worth, TX (US)

( * ) Notice: Subject to any disclaimer, the term of this patent is extended or adjusted under 35 U.S.C. 154(b) by 578 days.

This patent is subject to a terminal disclaimer.

(21) Appl. No.: 10/910,504

(22) Filed: Aug. 3, 2004

(65) Prior Publication Data

US 2005/0203034 A1 Sep. 15, 2005

Related U.S. Application Data

(60) Provisional application No. 60/552,682, filed on Mar. 12, 2004.

(51) Int. Cl.
A01N 43/04 (2006.01)
A61K 31/70 (2006.01)

(52) U.S. Cl. ..................................................... 514/30

(58) Field of Classification Search .................... None
See application file for complete search history.

(56) References Cited

U.S. PATENT DOCUMENTS

| | | | |
|---|---|---|---|
| 3,954,791 A | 5/1976 | Loewe et al. | |
| 3,993,682 A | 11/1976 | Kolling et al. | |
| 4,283,400 A | 8/1981 | von Bittera et al. | |
| 4,447,414 A | 5/1984 | Gay et al. | |
| 4,597,969 A * | 7/1986 | Maxfield et al. | 424/692 |
| 4,666,939 A | 5/1987 | Voege et al. | |
| 4,717,566 A | 1/1988 | Eckenhoff et al. | |
| 4,988,696 A | 1/1991 | Andrews et al. | |
| 5,036,069 A | 7/1991 | Andrews et al. | |
| 5,093,334 A | 3/1992 | Andrews et al. | |
| 5,536,715 A | 7/1996 | Hood | |
| 5,538,989 A | 7/1996 | Kyle | |
| 5,550,153 A | 8/1996 | Kerz | |
| 5,756,474 A | 5/1998 | Furstenau | |
| 5,824,653 A | 10/1998 | Beuvry et al. | |
| 5,840,324 A | 11/1998 | Hennessy et al. | |
| 5,861,142 A | 1/1999 | Schick | |
| 5,945,317 A | 8/1999 | Byrne et al. | |
| 6,201,012 B1 | 3/2001 | Lowndes et al. | |
| 6,207,179 B1 | 3/2001 | Mihalik | |
| 6,340,672 B1 | 1/2002 | Mihalik | |
| 6,383,471 B1 | 5/2002 | Chen et al. | |
| 6,492,340 B2 | 12/2002 | Mihalik | |
| 6,503,536 B2 | 1/2003 | Kalbe et al. | |
| 6,521,610 B2 | 2/2003 | Tiebes et al. | |
| 6,524,602 B1 | 2/2003 | Burkhart et al. | |
| 6,541,455 B2 | 4/2003 | Pearlman | |
| 6,552,002 B2 | 4/2003 | Steber et al. | |
| 6,562,363 B1 | 5/2003 | Mantelle et al. | |
| 6,596,714 B1 | 7/2003 | Mihalik | |
| 6,596,727 B1 | 7/2003 | Schaper et al. | |
| 6,605,595 B1 | 8/2003 | Omura et al. | |
| 6,617,314 B2 | 9/2003 | Grosse-Bley et al. | |
| 6,627,613 B2 | 9/2003 | Strobel | |
| 6,663,879 B2 | 12/2003 | Harvey | |
| 6,764,999 B2 | 7/2004 | Bachman et al. | |
| 6,858,601 B2 | 2/2005 | Mihalik | |
| 6,872,708 B2 | 3/2005 | Matsumoto et al. | |
| 6,903,052 B2 | 6/2005 | Williams et al. | |
| 2003/0055089 A1 | 3/2003 | Sirinyan et al. | |
| 2003/0068365 A1 | 4/2003 | Suvanprakorn et al. | |
| 2003/0077297 A1 | 4/2003 | Chen et al. | |
| 2003/0119852 A1 | 6/2003 | Beckmann et al. | |
| 2003/0144251 A1 | 7/2003 | Wu et al. | |
| 2003/0203891 A1 | 10/2003 | Goebel et al. | |
| 2003/0236203 A1 | 12/2003 | Freehauf et al. | |
| 2004/0006047 A1 | 1/2004 | Schaper et al. | |
| 2004/0018241 A1 | 1/2004 | Houze et al. | |
| 2004/0019062 A1 | 1/2004 | Mihalik | |
| 2004/0037869 A1 | 2/2004 | Cleverly et al. | |
| 2004/0043925 A1 | 3/2004 | Kalbe et al. | |
| 2004/0151744 A1 | 8/2004 | Bishop | |
| 2004/0162283 A1 | 8/2004 | Geobel et al. | |
| 2004/0180034 A1 | 9/2004 | Hughes et al. | |
| 2004/0224012 A1 | 11/2004 | Suvanprakorn et al. | |
| 2004/0234579 A1 | 11/2004 | Finke | |
| 2004/0234580 A1 | 11/2004 | Huber et al. | |
| 2005/0032718 A1 | 2/2005 | Burke et al. | |
| 2005/0032719 A1 | 2/2005 | Cottrell et al. | |
| 2005/0118241 A1 | 6/2005 | Landschaft | |
| 2005/0136087 A1 | 6/2005 | Freehauf | |

FOREIGN PATENT DOCUMENTS

| EP | 0 059 074 | 10/1984 |
|---|---|---|
| EP | 0 717 993 B1 | 3/2000 |
| GB | 2 252 730 B | 12/1994 |
| WO | WO 00/48636 | 8/2000 |

OTHER PUBLICATIONS

Parikh. Handbook of Pharmaceutical Granulation Technology, Drugs and the Pharmaceutical Sciences; 81, New York Marcel Dekker, Inc., 1997, pp. 51 and 52.*

* cited by examiner

Primary Examiner—Shaojia Anna Jiang
Assistant Examiner—Layla Bland
(74) Attorney, Agent, or Firm—Patterson & Sheridan, L.L.P.

(57) ABSTRACT

The present invention provides a method for preparing a pharmaceutical formulation containing ivermectin and a method and composition that can contain ivermectin plus tetrahydropyrimidines. An examples of a tetrahydropyrimidine includes pyrantel. A pharmaceutical formulation is provided for use in the treatment of helminthiasis of mammals, and particularly tapeworm, hookworm, roundworm and heartworm of domestic animals and farm animals. The present invention also provides a method of treating helminthiasis in mammals, which method comprises administering to the mammal in need thereof an anthelmintically effective amount of a pharmaceutical formulation of the invention.

22 Claims, No Drawings

MULTI-ACTION ANTHELMINTIC FORMULATIONS

CROSS REFERENCE TO RELATED APPLICATIONS

The present application is a continuation-in-part of Provisional U.S. Application No. 60/552,682, filed Mar. 12, 2004. Priority is claimed to the application listed above, which is incorporated herein by reference.

BACKGROUND OF INVENTION

The invention relates generally to anthelmintic formulations which can have significant parasiticidal activity as anthelmintics, ectoparasiticides, insecticides or acaricides in animal health and more particularly to solid anthelmintic formulations containing ivermectin.

Active ingredients of anthelmintics and their methods of formation in accordance with preferred embodiments of the invention are discussed in e.g. U.S. Pat. Nos. 3,502,661 and 4,199,569, the contents of which are incorporated herein by reference.

It is often beneficial, under certain circumstances, to include multiple drugs in the same formulation in order to target a wider variety of parasites. One particularly desirable anthelmintic active ingredient is ivermectin. Ivermectin is hygroscopic and therefore tends to be undesirably unstable. It has also been seen that ivermectin is unstable in both acidic and basic solutions and is susceptible to photodegradation and oxidative degradation. Accordingly, it is very difficult to prepare a solid composition, such as a tablet, containing ivermectin without having to resort to using a large amount of filler material to make up the bulk of the tablet in order to maintain the integrity of the compound. Even then, degradation problems can exist. This problem is compounded when additional drugs are intended to be included in the same formulation, as ivermectin can degrade other drugs.

Accordingly, it is desirable to provide a multidrug formulation in solid form that can be formed into a solid or tablet of optimal size, palatable to animals and which can be easily administered to the affected animal.

Another object of the invention is to provide an improved method of preparing formulations including ivermectin.

SUMMARY OF THE INVENTION

Generally speaking, in accordance with the invention, a pharmaceutical formulation is provided for use in the treatment animals, more particularly, in the treatment of helminthiasis of mammals, and more particularly tapeworm, hookworm, roundworm and heartworm of domestic animals or farm animals. Accordingly, the present invention provides a method of treating helminthiasis in mammals, which method comprises administering to the mammal in need thereof, an anthelmintically effective amount of a pharmaceutical formulation of the invention. The present invention also provides a composition and a method for preparing a pharmaceutical formulation containing an avermectin such as ivermectin and a method and composition that can contain ivermectin plus other active compositions such as anthelmintic pyrimidines such as tetrahydropyrimidines. Examples of a tetrahydropyrimidine include, for example, a pyrantel. Examples of a pyrantel include, for example, pyrantel pamoate. Formulations in accordance with the invention can remain stable for over one month, and typically, much longer.

One preferred method involves isolating the ivermectin through granulation, in particular, spray granulation. The other actives (drugs) can also be granulated or spray granulated. The granules can be left in a powder form, tabletted, encapsulated or otherwise dealt with. One method of preparation of the formulation comprises the following steps:

(a) preparing a first and second (or more) combination including the first and second active ingredient, respectively;

(b) combining the combination from (a) with diluents to form one or two separate solutions;

(c) granulating one or all of the solutions from (b), especially by spray granulation, by combining with a dry combination;

(d) drying the resulting granules, if needed;

(e) blending the granules from (d), which contain the first and second active ingredients and an excipient combination; and (f) forming the blended granules into tablets or capsules or leaving in powder form.

DETAILED DESCRIPTION OF THE PREFERRED EMBODIMENTS

The present invention relates to anthelmintic active compound combinations including avermectins and anthelmintic pyrimidines such as tetrahydropyrimidines. Acceptable tetrahydropyrimidines include, for example, pyrantel, morantel and oxantel. Acceptable pyrantels include, for example, pyrantel pamoate. Acceptable avermectins include, for example, ivermectin, doramectin, selamectin and abamectin.

A formulation of active ingredients comprising ivermectin and pyrantel is particularly preferred. The active ingredients target different pathogenic organisms that can adversely affect the health of a mammal. This particular combination is particularly effective in fighting a wide variety of organisms. However, administering two physically separate pharmaceutical compositions to an animal is undesirable. It has been determined that it would be beneficial to combine the active ingredients into one formulation, in particular, one tablet (or capsule) containing a pharmaceutically effective amount of the active ingredients, thereby decreasing the number of administrations of therapeutic formulations to the animal.

The disease or group of diseases described generally as helminthiasis is due to infestation of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. Repeat treatments are given as required to combat re-infestations and are dependent upon the species of parasite. The techniques for administering these materials to animals are known to those skilled in the field of veterinary medicine.

The preparations are suitable for combating pathogenic endoparasites which occur in animal husbandry and animal breeding in productive, breeding, zoo, laboratory, experimental animals and pets, and have a favorable toxicity to warm-blooded animals. In this connection, they are active against all or individual stages of development of the pests and against resistant and normally sensitive species. By combating pathogenic endoparasites, it is intended that disease, cases of death and reduction in production (for example in the production of meat, milk, wool, hides, eggs, etc.) are reduced so that more economic and simpler animal husbandry is possible by means of the use of the pharmaceutical formulation.

The productive and breeding animals include mammals, such as, for example, cattle, horses, sheep, pigs, goats, camels, water buffalo, donkeys, rabbits, fallow deer and reindeer, pelt animals, such as, for example, mink, chinchilla and raccoons, birds, such as, for example, chickens, geese, turkeys and ducks, fresh and salt-water fish, such as, for example, salmon, trout, carp and eels, and reptiles.

Laboratory and experimental animals include mice, rats, guinea pigs, hamsters, dogs and cats.

Pets include dogs and cats, as well as mice, rats, guinea pigs, hamsters and so forth.

The formulation according to the invention is particularly effective when administered to dogs and cats, but is suitable for other mammals.

Administration can take place both prophylactically and therapeutically.

The formulations can be administered directly or in the form of suitable preparations, enterally, parenterally or dermally.

Enteral administration of the formulations takes place, for example, orally in the form of powder, tablets, capsules, pastes, potions, granules, orally administered solutions, suspensions and emulsions, boli, medicated feed or drinking water.

Suitable preparations are:
  oral solutions and concentrates for oral administration after dilution;
  emulsions and suspension for oral administration; and semisolid preparations;
  formulations in which the active compound is processed in an ointment base or in an oil-in-water or water-in-oil emulsion base;
  solid preparations, such as powders, premixes or concentrates, granules, pellets, tablets, caplets, boli and capsules, with tablets the preferred form;
  oral solutions are prepared by dissolving the active compound in a suitable solvent and, if appropriate, adding additives such as solubilizers, acids, bases, buffer salts, antioxidants and preservatives. The solutions are filtered and packed under sterile conditions.

Solvents may include: physiologically acceptable solvents, such as water, alcohols, such as ethanol, butanol, methanol, benzyl alcohol and isopropanol, glycerol, propylene glycol, polyethylene glycol, N-methylpyrrolidone, and mixtures of the same.

The active compounds can, if appropriate, also be dissolved in physiologically acceptable vegetable or synthetic oils.

Solubilizers may include: solvents which promote dissolution of the active compound in the main solvent or substances which prevent precipitation of the active compound. Examples are polyvinyl pyrrolidone, polyoxyethylated castor oil and polyoxyethylated sorbitan esters.

One particularly preferred formulation of the invention, comprising two active ingredients, is preferably administered in the form of capsules, more preferably tablets. A preferred formulation of the present invention contains 0.005-25% ivermectin, preferably 0.01-15%, and most preferably 0.012-5%, with 0.023% as a preferred example. A preferred formulation of the present invention can contain 1.5-76% of an anthelmintic pyrimidine, preferably pyrantel, more preferably pyrantel pamoate, preferably 6-52%, and most preferably 11.2-23%, with 19.0% as a preferred example. All percentages for pyrantel or pyrantel pamoate are given as the pyrantel base. All percentages herein, unless otherwise evident, are on a weight basis. As used herein, unless indicated otherwise, the percentages are based on the entire formulation, including carriers, excipients and so forth.

A preferred ratio range of pyrantel to ivermectin is 500-1000:1, and most preferably 700-900:1, with 826:1 pyrantel to ivermectin as a preferred example.

A preferred dosage of avermectin, e.g., ivermectin, is about 5-7 µg/Kg body weight of the animal administered monthly, preferably 5.5-6.5 µg/Kg body weight, with 6 µg/Kg body weight as a preferred example. A preferred dosage of anthelmintic pyrimidines, e.g., pyrantel, is about 4.25-5.75 mg/Kg body weight administered monthly, preferably 4.75-5.25 mg/Kg, with 5 mg as a preferred example. In accordance with the invention, this dosage would be contained in a single administration, such as in one or two tablets or capsules or in a single packet.

To prepare solid preparations, the active compound should be mixed with suitable excipients, if appropriate, with addition of auxiliaries, and converted to the form desired.

One preferred method of preparation of the formulation comprises the following steps:
  (a) preparing a first and a second (or more) preparation including the first and second active ingredient, respectively;
  (b) combining the preparation from (a) with diluents to form one or two separate solutions;
  (c) granulating one or all of the diluted preparations from (b), especially by spray granulation, by combining with a dry combination;
  (d) drying the resulting granules, if needed;
  (e) blending the granules from (d), which contain the first and/or second active ingredients with an excipient combination; and
  (f) forming the blended granules into tablets or capsules or leaving in powder form.

Spray granulation can involve the spraying of liquid (i.e., solution, suspension, dispersion, melt and so forth) onto a powder or granules while simultaneously building particle size and removing the volatile liquid by drying. By mixing an active ingredient with a carrier in the liquid phase, the active can become "encapsulated" or substantially covered in a matrix of carrier after the spray granulation process. Granulation is generally performed by spraying liquid into the fluidized powder. The granules can subsequently be dried with heated air.

In one embodiment of the invention, a solution, slurry, melt or the like, or a combination of these, comprising liquid, active ingredient and excipient material, is sprayed. Spraying helps remove the unneeded liquid and results in the formation of granules. The granules comprise both active ingredient and excipient materials. These granules can be further dried as needed.

The presence of acid in the final formulation can decrease the stability of ivermectin. Formulations using water solvents can also include citric acid, which may have an undesirable effect on ivermectin stability. Also, it is not always possible to remove all of the water in the drying step of making the formulation. The trace amount of water could accelerate the degradation of the ivermectin. To overcome these limitations the formulation may be made using a solvent such as an alcohol, instead of water, said formulation not containing citric acid. It is often easier to remove non-aqueous solvents, for example ethanol and isopropanol, under mild conditions. Thus, a non-aqueous preparation can lead to a final product having improved properties compared to a final product having retained water.

Suitable excipients may include physiologically acceptable inert solids such as, for example, sodium chloride, calcium carbonate, hydrogen carbonates, aluminum oxides, silicas, clays, precipitated or colloidal silicon dioxide and phosphates. Other suitable excipients may include, for example, sugar, cellulose, Croscarmellose Sodium (i.e., carboxymethyl cellulose), Aerosil, nutrients and feedstuffs, such as milk powder and pork liver powder, animal meals, ground and crushed cereal meals, Avicel PH102 and starches.

Auxiliaries can include preservatives, antioxidants and colorants. Additional suitable auxiliaries can include lubricants, such as, for example, magnesium stearate, stearic acid, talcum and bentonites, disintegration-promoting substances, such as starch or transversely crosslinked polyvinyl pyrrolidone, binders, such as, for example, starch, gelatin or linear polyvinyl pyrrolidone, and dry binders, such as microcrystalline cellulose.

The formulation can also be in the form of a chewable, such as a beef-chewable containing ground or minced beef or other meat, in addition to other excipients listed above.

The materials in the final formulation, such as the excipients, auxiliaries, synergists and other materials, which aid in delivery, shelf-life, desired physical structure and so forth will be referred to herein generally as carrier material. As stated herein, carrier material could be pharmaceutically active under certain circumstances.

As used herein, the identification of an active ingredient, e.g. a tetrahydropyrimidine or ivermectin, is intended to cover pharmaceutically active forms thereof such as salts, hydrochlorides, chelates, and so forth.

The following example is given for purposes of illustration only and is not intended to be construed in a limiting manner.

EXAMPLE 1

Preparation of Tablets or Caplets Containing Ivermectin and Pyrantel

Three separate mixtures were prepared as follows:
Mixture A:

TABLE 1

| Ingredient | Amount (g) | % w/w |
| --- | --- | --- |
| Ivermectin | 65 | 0.028 |
| Microcrystalline Cellulose USP (Avicel PH102) | 17,082 | 7.28 |
| Polyvinylpyrrolidone (Povidone K30) | 13,860 | 5.91 |
| Croscarmellose Sodium | 5,530 | 2.36 |
| Polyethylene Glycol 8005 | 3,500 | 1.50 |
| Citric Acid Anhydrous | 71 | 0.03 |
| Sodium Citrate Dihydrate | 24.5 | 0.01 |
| Purified Water | 12,165 | |

The ingredients were dispensed in the amounts specified in Table 1. The percentages are based on the percentage found in the final combined multi-action therapeutic formulation.

The following materials (in the order listed below) were passed through a Russel Sieve fitted with 20# sieve and collected in a stainless steel drum:

(a) Avicel PH102
(b) Croscarmellose Sodium
(c) Povidone

The delumped material resulting from the step above was added to the drum tumbler and blended for 20 minutes. Purified water was added to a stock pot with citric acid and sodium citrate dihydrate. The contents were mixed for 5 minutes with a stirring rod.

Polyethylene glycol flakes were added to a separate stock pot and heated with a water bath to a temperature of 50-65° C. to melt the flakes. The solution was maintained at this temperature. Ivermectin was added to the melted polyethylene glycol with gentle stirring until the compound was dissolved. The solution was maintained at 50-65° C.

95.5 g of the citrate salts dissolved in 165 g of purified water was added to the melted polyethylene glycol/ivermectin solution and stirred with gentle agitation for at least 5 minutes until the solution was clear. The stirring was then ceased to allow any air bubbles to escape and the solution was maintained at 50-65° C.

The remaining citrate buffer solution was placed on a hot plate and heated to a temperature of 55±5° C.

The blended Avicel, Croscarmellose Sodium and Povidone was transferred to a spray granulator. The solutions were spray granulated as follows:

(a) The spray granulator was programmed with the following parameters:
  (1) inlet air temperature: 50±10° C.
  (2) outlet air temperature: 45±10° C.
  (3) bed temperature: 43±10° C.
  (4) atomization pressure: 3-5 bar
  (5) spray rate: 100 g±20 g per minute
  (6) pan speed: 2-10 rpm
(b) The ivermectin/polyethylene glycol/citrate buffer solutions was sprayed at a rate of 100±20 g/minute until all of the solution was sprayed.
(c) The reserve citrate buffer at 55±5° C. was added to the container which held the previous solution for rinsing purposes. The rinse citrate buffer was sprayed at a rate of 100±20 g/minute.
(d) Granulation was continued by spraying the remaining purified water (1000 g) at room temperature. Additional purified water (200 g) was sprayed until the desired consistency was achieved.

The granules were then emptied into the drying bowl and dried using a fluid bed drier. After drying, the bowl was removed and the granules were mixed with a scoop. The dried granules obtained were transferred in double polythene lined suitable container.

TABLE 2

| Ingredient | Amount (g) | % w/w |
| --- | --- | --- |
| Pyrantel Pamoate | 126,485 | 53.90 |
| Avicel PH102 | 14,656 | 6.25 |
| Croscarmellose Sodium | 5,239 | 2.23 |
| Povidone K30 | 4,075 | 1.73 |

The ingredients were dispensed in the amounts specified in Table 2.

The following materials (in the order listed below) were passed through a Russel Sieve fitted with 20# sieve and collected in a suitable container:
(a) Pyrantel Pamoate
(b) Povidone
(c) Croscarmellose Sodium
(d) Avicel PH102

The sieved material was added to a Diosna mixer and blended for 10 minutes using the impeller on low speed with the chopper off. The mixture was granulated with 9,000 g of purified water with the impeller and the chopper set on low speed. Additional purified water was added to achieve the good granular mass.

The granulated mixture was dried using a fluid bed drier and transferred to a double polythene lined suitable container.

Excipient Mixture:

TABLE 3

| Ingredient | Amount (g) | % w/w |
|---|---|---|
| SD Pork Liver Powder | 17,972 | 7.66 |
| Avicel PH102 | 16,356 | 6.97 |
| Croscarmellose Sodium | 6,100 | 2.60 |
| Aerosil | 693 | 0.30 |
| Magnesium Stearate | 2,888 | 1.23 |

The ingredients were dispensed in the amounts specified in Table 3.

The first four excipients were sifted through a 500# sieve and collected in a suitable container. Then the Magnesium Stearate was sifted through a 500# mesh sieve. The two mixtures containing the active ingredients of the formulation (i.e., Mixtures A and B) and the excipient mixture were blended in a drum tumbler for 25 minutes. The sifted Magnesium Stearate was added and blended for an additional 5 minutes.

The formulation was then either compressed into tablets or caplets of 300 mg, 600 mg or 1200 mg or the granules were packaged into sachets.

EXAMPLE 2

Preparation of Tablets or Caplets Containing Ivermectin and Pyrantel

Three separate mixtures were prepared as follows:

TABLE 4

| Ingredient | Amount (Kg) | % w/w |
|---|---|---|
| Ivermectin | 0.065 | 0.028 |
| Avicel PH102 | 17.082 | 7.39 |
| Povidone K30 | 13.860 | 6.00 |
| Croscarmellose Sodium | 5.530 | 2.39 |
| Ethyl Alcohol (99% USP) | 36.537 | |

The ingredients were dispensed in the amounts specified in Table 4.

The following materials (in the order listed below) were passed through a Russel Sieve fitted with a 20# sieve and collected in a stainless steel drum:
(a) Avicel PH102
(b) Croscarmellose Sodium
(c) Povidone The delumped material resulting from the step above was added to the drum tumbler and blended for 20 minutes.

1.750 Kg of ethyl alcohol was added to a flask. The ivermectin was gradually added to the ethyl alcohol under constant stirring until the ivermectin was completely dissolved. The ivermectin solution was diluted with 8.415 Kg of ethyl alcohol under gentle stirring. The solution was stirred for an additional 30 minutes.

The blended Avicel, Croscarmellose Sodium and Povidone was transferred to a spray granulator. The solutions were spray granulated as follows:
(a) The spray granulator was programmed with the following parameters:
(1) inlet air temperature: 50±10° C.
(2) outlet air temperature: 45±10° C.
(3) bed temperature: 43±10° C.
(4) atomization pressure: 3-5 bar
(5) spray rate: 100 g±20 g per minute
(6) pan speed: 2-10 rpm
(b) The ivermectin solution and the Avicel/Croscarmellose Sodium/Povidone blend were sprayed at a rate of 100±20 g/minute until all of the solution was sprayed.
(c) The container was rinsed with the remaining 2 Kg of ethyl alcohol. The rinse was then sprayed at a rate of 100±20 g/minute until all of the solution was sprayed.

Once spraying was complete, the wet mass was granulated for 10 minutes. The granules were then emptied into the drying bowl and dried using a fluid bed drier. After drying, the bowl was removed and the granules were mixed with a scoop. The dried granules obtained were passed through a Russel sieve fitted with the 12# sieve. The dried material was then transferred to a suitable container.

TABLE 5

| Ingredient | Amount (Kg) | % w/w |
|---|---|---|
| Pyrantel Pamoate | 126.485 | 54.75 |
| Avicel PH102 | 14.656 | 6.34 |
| Croscarmellose Sodium | 5.239 | 2.27 |
| Povidone K30 | 4.075 | 1.76 |
| Isopropyl Alcohol | 50.00 | |

The ingredients were dispensed in the amounts specified in Table 5.

The following materials (in the order listed below) were passed through a Russel Sieve fitted with 20# sieve and collected in a suitable container:
(a) Pyrantel Pamoate
(b) Povidone
(c) Croscarmellose Sodium
(d) Avicel PH102

The sieved material was added to a Diosna mixer and blended for 10 minutes using the impeller on low speed with the chopper off. The mixture was granulated with 25 Kg of isopropyl alcohol with the impeller on low speed for 5 minutes and the choppers off. The granulated material was then mixed for an additional 4 minutes to achieve good granules with the choppers on.

After the granulation endpoint was obtained, the walls of the Diosa were scraped and the wet mass was unloaded into a drying bowl. The granulated mixture was dried using a fluid bed drier and then mixed with a scoop. The dried granules obtained were passed through a Russel sieve fitted with the 12# sieve. The dried material was then transferred to a suitable container.

Excipient Mixture:

TABLE 6

| Ingredient | Amount (Kg) | % w/w |
|---|---|---|
| SD Pork Liver Powder | 17.972 | 7.78 |
| Avicel PH102 | 16.356 | 7.08 |
| Croscarmellose Sodium | 6.100 | 2.64 |
| Aerosil 200 | 0.693 | 0.30 |
| Magnesium Stearate | 2.888 | 1.25 |

The ingredients were dispensed in the amounts specified in Table 6.

The first four excipients were sifted through a 5 W sieve and collected in a suitable container. Then the Magnesium Stearate was sifted through a 500# mesh sieve. The two mixtures containing the active ingredients of the formulation (i.e., Mixtures C and D) and the excipient mixture were blended in a double cone blender for 25 minutes. The sifted Magnesium Stearate was added and blended for an additional 5 minutes.

The formulation was then either compressed into tablets or caplets of 300 mg, 600 mg or 1200 mg or the granules were packaged into sachets.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween. Particularly it is to be understood that in said claims, ingredients or compounds recited in the singular are intended to include compatible mixtures of such ingredients wherever the sense permits.

What is claimed is:

1. A method for forming an anthelmintic formulation comprising the steps of:
   preparing a combination of ivermectin, an alcohol, and a second material, wherein the second material comprises polyethylene glycol; then
   spray granulating the combination to form granules, with the polyethylene glycol covering the ivermectin, and
   combining the granules with an additional active ingredient composition.

2. The method of claim 1, wherein the additional ingredient composition consists essentially of a pyrantel or pyrantel pamoate.

3. The method of claim 1, comprising adding an anthelmintic pyrimidine to the formulation.

4. The method of claim 1, wherein the formulation is pressed into a tablet or enclosed in a capsule and the ivermectin has been effectively isolated, so that the formulation will stay stable for over one month.

5. The method of claim 1, wherein the spray granulating step maintains the ivermectin stable for over one month.

6. A method for forming an anthelmintic formulation, comprising the steps of:
   a) preparing a first preparation comprising an avermectin, polyethylene glycol, and water;
   b) preparing a second preparation comprising a tetrahydropyrimidine and water, wherein the avermectin and tetrahydropyrimidine preparations together comprise an anthelmintic combination
   c) separately forming solids from the first and second preparations, said solid forming step comprising spray granulating the first preparation with the polyethylene glycol covering the avermectin; and
   d) combining the solid preparations to form an anthelmintic solid, consisting essentially of the avermectin and the tetrahydropyrimidine, with one or more appropriate excipients to provide the combinations in a form suitable to be administered to a mammal.

7. The method of claim 6, wherein the anthelmintic combination comprises ivermectin.

8. The method of claim 6, wherein the anthelmintic combination comprises at least about 0.005% ivermectin.

9. The method of claim 6, wherein the anthelmintic combination comprises about 0.012-5% ivermectin.

10. The method of claim 6, wherein the anthelmintic combination comprises pyrantel pamoate.

11. The method of claim 6, wherein the anthelmintic combination comprises at least about 1.5% pyrantel pamoate.

12. The method of claim 6, wherein the anthelmintic combination comprises about 11.2-23% pyrantel pamoate.

13. The method of claim 6, wherein the solid forming step comprises spray granulating ivermectin.

14. A method for forming an anthelmintic formulation comprising the steps of:
   a) preparing a first preparation comprising an avermectin, polyethylene glycol and an alcohol;
   b) preparing a second preparation comprising a tetrahydropyrimidine and an alcohol, wherein the avermectin and tetrahydropyrimidine preparations together comprise an anthelmintic combination
   c) separately forming solids from the first and second preparations, said solid forming step comprising spray granulating the first preparation with the polyethylene glycol covering the avermectin; and
   d) combining the solid preparations to form an anthelmintic solid, consisting essentially of the avermectin and the tetrahydropyrimidine, with one or more appropriate excipients to provide the combinations in a form suitable to be administered to a mammal.

15. The method of claim 14, wherein the anthelmintic combination comprises ivermectin.

16. The method of claim 14, wherein the anthelmintic combination comprises at least about 0.005% ivermectin.

17. The method of claim 14, wherein the anthelmintic combination comprises about 0.012-5% ivermectin.

18. The method of claim 14, wherein the anthelmintic combination comprises pyrantel pamoate.

19. The method of claim 14, wherein the anthelmintic combination comprises at least about 1.5% pyrantel pamoate.

20. The method of claim 14, wherein the anthelmintic combination comprises about 11.2-23% pyrantel pamoate.

21. The method of claim 14, wherein the alcohol is selected from the group consisting of ethanol, butanol, benzyl alcohol, and isopropanol.

22. The method of claim 14, wherein the solid forming step comprises spray granulating ivermectin.

* * * * *

UNITED STATES PATENT AND TRADEMARK OFFICE
CERTIFICATE OF CORRECTION

PATENT NO. : 7,582,612 B2
APPLICATION NO. : 10/910504
DATED : September 1, 2009
INVENTOR(S) : Ahn et al.

It is certified that error appears in the above-identified patent and that said Letters Patent is hereby corrected as shown below:

Column 6, Line 57, please insert --Mixture B:-- above Table 2;

Column 7, Line 46, please insert --Mixture C:-- above Table 4;

Column 8, Line 32, please insert --Mixture D:-- above Table 5.

Signed and Sealed this

Fourteenth Day of September, 2010

David J. Kappos
*Director of the United States Patent and Trademark Office*